(12) United States Patent
Boivin et al.

(10) Patent No.: US 9,709,472 B2
(45) Date of Patent: Jul. 18, 2017

(54) FLUXER HAVING A MODULAR ELECTRICALLY POWERED FURNACE

(71) Applicant: SPEX Sample Prep, LLC, Metuchen, NJ (US)

(72) Inventors: Marc Boivin, Wendake (CA); Pierre-Emmanuel LeMay, Quebec (CA); Antoine Fiala, St-Romuald (CA); Marco Bernier, Riviere-du-Loup (CA)

(73) Assignee: SPEX SAMPLE PREP, LLC, Metuchen, NJ (US)

( * ) Notice: Subject to any disclaimer, the term of this patent is extended or adjusted under 35 U.S.C. 154(b) by 0 days.

(21) Appl. No.: 15/131,071

(22) Filed: Apr. 18, 2016

(65) Prior Publication Data

US 2016/0305858 A1    Oct. 20, 2016

Related U.S. Application Data

(60) Provisional application No. 62/148,229, filed on Apr. 16, 2015.

(51) Int. Cl.
| | |
|---|---|
| *G01N 1/44* | (2006.01) |
| *F27B 17/00* | (2006.01) |
| *F27B 17/02* | (2006.01) |
| *G01N 23/00* | (2006.01) |
| *F27D 5/00* | (2006.01) |

(52) U.S. Cl.
CPC ........... *G01N 1/44* (2013.01); *F27B 17/0016* (2013.01); *F27B 17/02* (2013.01); *G01N 23/00* (2013.01); *F27B 2017/0091* (2013.01); *F27D 2005/0075* (2013.01)

(58) Field of Classification Search
CPC ...... G01N 1/44; G01N 23/00; F27B 17/0016; F27B 17/02; F27B 2017/0091; F27D 2005/0075

USPC ....................................................... 73/863.11
See application file for complete search history.

(56) References Cited

U.S. PATENT DOCUMENTS

| | | | | |
|---|---|---|---|---|
| 4,329,136 | A | * 5/1982 | Willay | ............... G01N 23/2202 425/174.8 R |
| 4,609,392 | A | * 9/1986 | Claisse | ................... F27B 14/10 65/134.4 |
| 4,738,618 | A | * 4/1988 | Massey | ................... C30B 35/00 414/940 |
| 5,215,718 | A | 6/1993 | Katzer et al. | |
| 5,315,091 | A | * 5/1994 | O'Brien | .................. F27B 17/02 164/136 |

(Continued)

FOREIGN PATENT DOCUMENTS

| | | |
|---|---|---|
| CN | 203274493 U | 11/2013 |
| DE | 19506503 C1 | 9/1996 |
| WO | 2015128522 A1 | 9/2015 |

OTHER PUBLICATIONS

Authorized Officer: Lee W. Young, "International Search Report and Written Opinion", dated Jul. 15, 2016, issued in counterpart PCT Application No. PCT/US16/28030.

*Primary Examiner* — Lisa Caputo
*Assistant Examiner* — Nathaniel T Woodward
(74) *Attorney, Agent, or Firm* — Kaplan Breyer Schwarz, LLP

(57) ABSTRACT

A fluxer includes a single, wide furnace enclosure that is sufficiently large and prewired to accommodate multiple fusion positions. The furnace includes at least one movable insulated partition that defines the actual insulated volume of the furnace.

20 Claims, 12 Drawing Sheets

(56) References Cited

U.S. PATENT DOCUMENTS

| | | | | |
|---|---|---|---|---|
| 5,559,826 A | * | 9/1996 | Ohtani | F27B 17/0025 219/406 |
| 6,074,205 A | * | 6/2000 | Myburgh | F27B 17/02 373/118 |
| 6,305,930 B1 | * | 10/2001 | Fedak | F27B 9/00 34/209 |
| 2011/0113872 A1 | * | 5/2011 | Dejmek | B01J 19/0046 73/114.75 |
| 2011/0154858 A1 | * | 6/2011 | Prossor | C03B 5/06 65/21.5 |
| 2012/0051387 A1 | * | 3/2012 | Boivin | F27B 17/0016 373/134 |
| 2015/0093712 A1 | * | 4/2015 | Forest | F27B 7/08 432/253 |

* cited by examiner

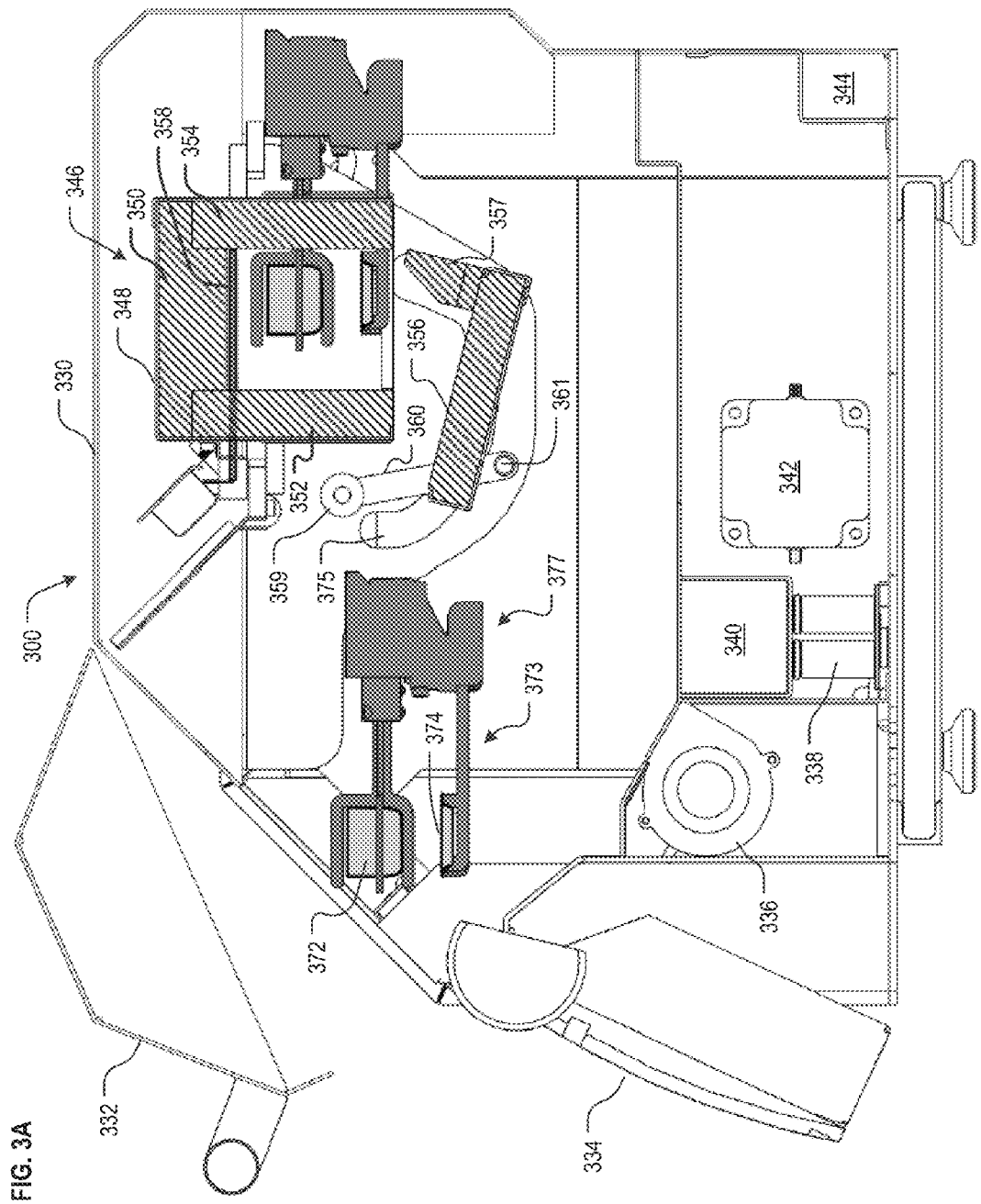

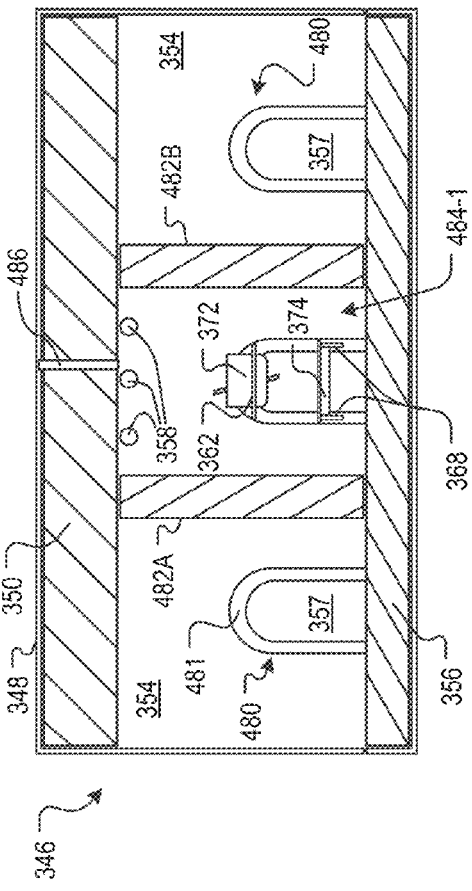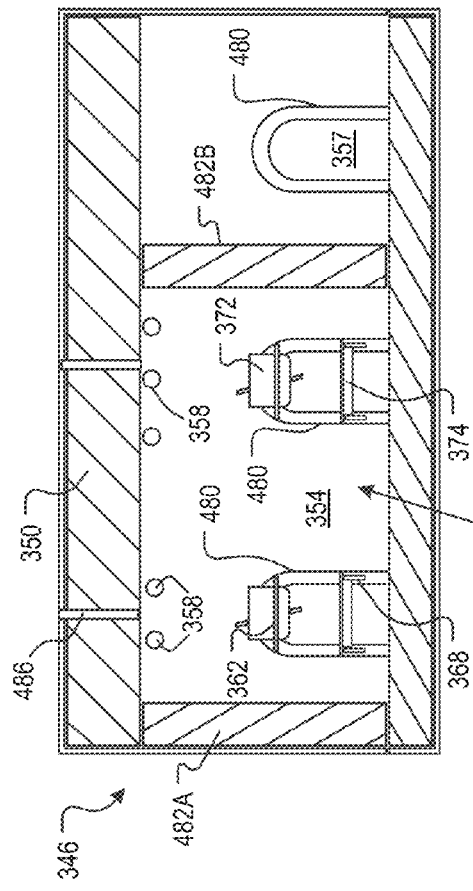

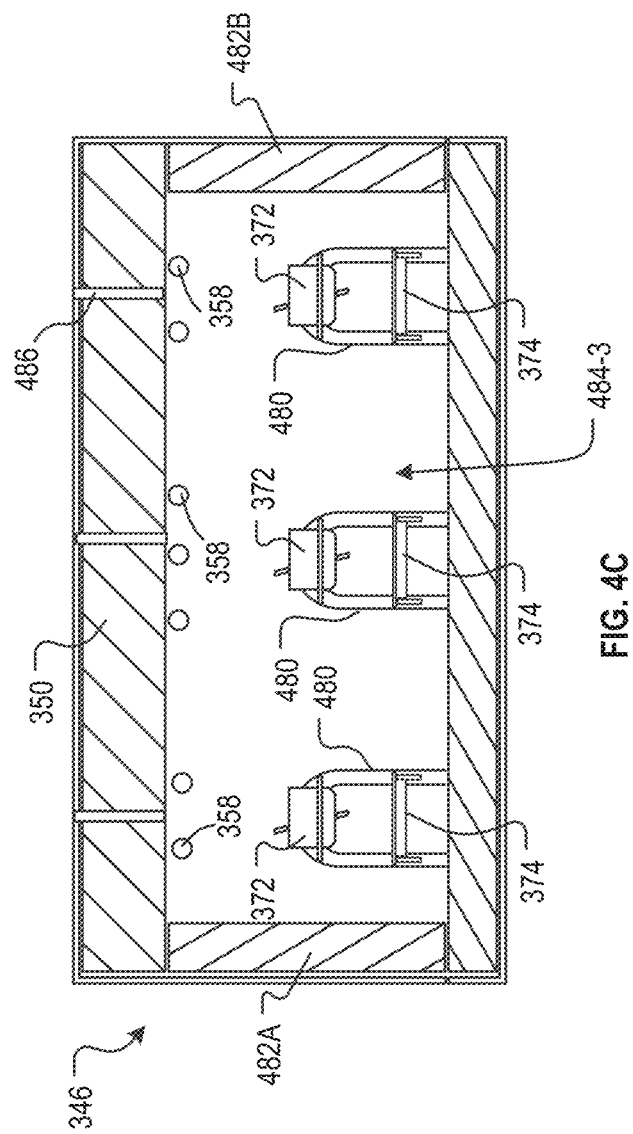

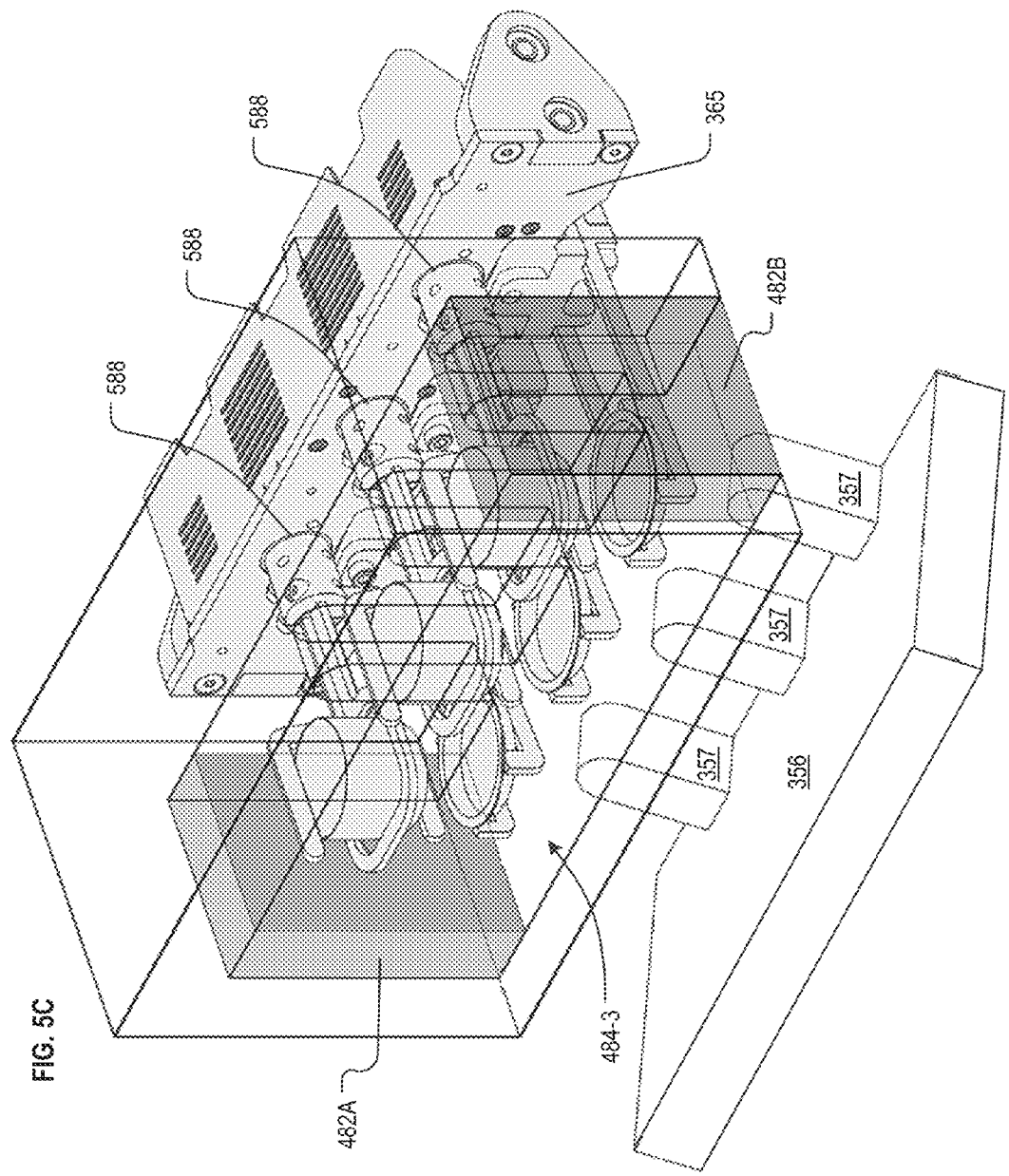

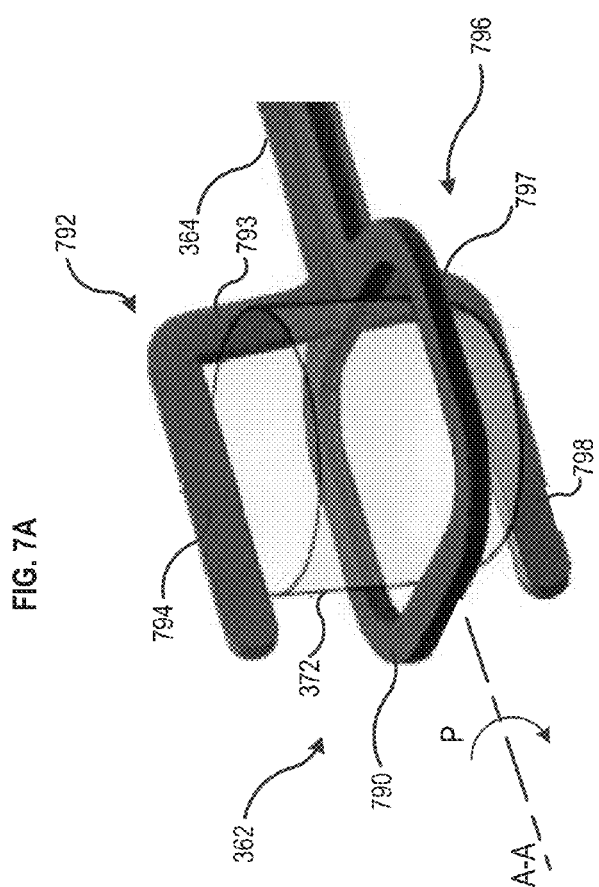
FIG. 7A
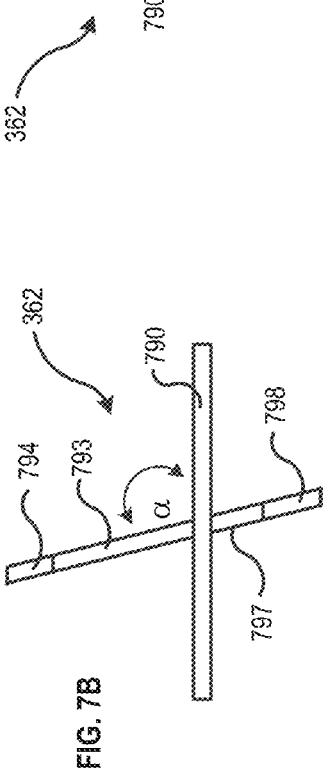
FIG. 7B
FIG. 7C

FLUXER HAVING A MODULAR ELECTRICALLY POWERED FURNACE

STATEMENT OF RELATED CASES

This case claims priority to U.S. patent application Ser. No. 62/148,229 filed Apr. 16, 2015 and incorporated by reference herein.

FIELD OF THE INVENTION

The present invention relates generally to the preparation of inorganic samples by fusion, and more particularly to a system and methods for doing so.

BACKGROUND

Analyzing an inorganic sample via analytical techniques such as x-ray fluorescence (XRF), inductively coupled plasma (ICP), atomic absorption (AA) requires that the sample be specially prepared before analysis. The sample must often be in the form of a homogeneous, solid, smooth-surface shape, such as that of a disk or bead. In this form, the sample does not exhibit mineralogical, grain-size, or orientation effects that might otherwise skew the analytical results.

A process known as "fusion" can be used to prepare samples for XRF, ICP, and AA. During the fusion process, a powdered sample is dissolved in a solvent, typically a lithium borate flux. The flux is solid at room temperature and must therefore be liquefied, which typically occurs at high temperature (c.a. 900 to 1000° C.).

As a consequence of the high temperatures required, the fusion process is performed in a heater/furnace/burner. Energy for the process is supplied either by gas (i.e., a gas burner) or electricity (i.e., an electric heater or furnace). Electrically powered furnaces can be inductive or resistive.

The heater or furnace, along with other control circuitry, etc., is contained with a larger enclosure; the assemblage is typically called a "fluxer".

"Platinumware" holders, including a "crucible holder" and a "mold holder" or "mold rack" are used in conjunction with the fluxer. The moniker "platinumware" derives from the fact that the crucibles and molds are typically made of platinum. FIG. 1 and FIG. 2 depict respective prior-art crucible holder 100 and mold rack 200, as used in some resistive-heated furnaces available from Katanax, Inc. of Québec, Canada. The platinumware holders are arranged to move in and out of the hot zone (i.e., furnace or burner flame) under the control of a motor/actuator.

Crucible holder 100 is capable of supporting plural crucibles 112. In the embodiment shown, crucible holder 100 is designed to accommodate five crucibles 112. As depicted in FIG. 1, crucible holder 100 includes support beam 102, spacers 104, retaining beams 106, brackets 108, and end shafts 110, arranged and interrelated as shown. Mold rack 200 is capable of supporting plural molds 224, which is typically consistent with the number of crucibles 112 in the crucible holder. Mold rack 200 includes support beams 214, mold retainers 216, spacers 218, brackets 220, and end supports 222, arranged and interrelated as shown.

In use, crucible holder 100 is disposed above molder holder 200. Crucible holder is supported so as to be rotatable about its longitudinal axis (i.e., an axis that aligns with the two end shafts 110). Crucibles 112 and molds 224 are situated to align with one another so that hot solution poured from each crucible 112 is received by a respective mold 224.

To begin the fusion process, the flux and sample are deposited into crucibles 112, which are then moved into the furnace cavity to begin the fusion process. See, e.g., http://www.katanax.com/cgi/show.cgi?products/K2prime/K2primevideo.I=en.html.

After the flux is liquefied, and after complete dissolution of the sample, the molten solution in the crucible(s) is poured into the plate-shaped platinum mold(s). Cooling results in a small, homogeneous glass-like disk or bead of sample, now suitable for analysis.

The throughput required of a fluxer will of course vary from one customer/lab/site (hereinafter "site") to another. And the requirements at a given site can change over time. In particular, with the increasing popularity of the fusion technique, it is likely that a site will see their fusion demands increase over time. Although some gas-fired fluxers are designed with a larger casing to accommodate a variable number of burners, no electrical fluxer offers this flexibility.

In particular, when designing gas fluxers, it is relatively easy to provide a manifold with multiple gas outputs, each one capable of functioning as a fusion position. To reduce the number of fusion positions, one or more of the gas outputs are capped or plugged. To increase the number of fusion positions, one or more burners are coupled to the gas outputs. The burners are typically positioned quite close one to another, so there is not much cost to providing the potential for a large capacity, even if a number of the fusion positions remain unused.

The issue of spare capacity is more complicated with electric fluxers. If a large furnace is built, all heating elements must be operated to provide the requisite heating, even if only a few samples are being processed such that spare capacity remains. Alternatively, a fluxer could be designed to accommodate several individual furnaces situated adjacent to one another. But since each furnace requires several inches of insulation, when positioned side-by-side, the thickness of the (insulated) side walls widens the fluxer to an unacceptable size.

To satisfy increasing fusion demands, it is advantageous to conduct the fusion process as quickly as possible. This implicates the fluxer's temperature response; that is, the relative speed with which it is capable of changing temperature and stabilizing at temperature targets. Despite its many benefits, a perceived drawback of a typical electric fluxer is that its temperature cannot vary as quickly as that of a gas fluxer.

As a consequence, there is a need for an electric fluxer that can accommodate an increase in the number of fusion positions (i.e., the number of simultaneous samples that can be accommodated per run). This would enable an initial modest throughput to be increased without having to purchase a new fluxer. Furthermore, there is a need for an electric fluxer with increased temperature responsivity, which will speed the fusion process thereby increasing throughput.

SUMMARY

The present invention provides a way to address the aforementioned shortcomings of electric fluxers. The illustrative embodiment of the invention is a fluxer having a modular electric "fusion" furnace.

A fluxer in accordance with the present teachings includes a single, wide furnace enclosure that is sufficiently large and prewired to accommodate multiple fusion positions. The furnace includes at least one movable insulated partition that defines the actual insulated volume of the furnace (i.e., the furnace cavity). In the illustrative embodiment, the furnace accommodates a maximum of three fusion positions and includes two movable insulated partitions. The term "insulated" and inflected forms thereof, as used in this disclosure and the appended claims, means thermally insulated. The partitions can be sited at four different positions (i.e., one position at either end of the furnace enclosure and two intermediate positions that divide the enclosure into thirds). Three heating elements are disposed across the top of the furnace spanning the middle third of the furnace enclosure (i.e., the central fusion position).

Placing one movable partition at each of the two intermediate positions defines a small heated furnace cavity that covers the middle third of the furnace enclosure. This provides a single fusion position. Moving one of the partitions from the intermediate position to the nearest end of the furnace enclosure enlarges the insulated cavity to encompass two fusion positions. And moving both partitions, one each to opposite ends of the furnace enclosure enlarges the insulated volume to the full size of the furnace enclosure to accommodate three fusion positions. Thus, by virtue of the movable insulated partitions, a variable size furnace cavity is created.

Each enlargement of the insulated cavity beyond a single fusion position requires additional parts. In the illustrative embodiment, for each additional fusion position, two heating elements, a crucible-holder assembly, and mold-holder assembly are added (among other parts).

The use of movable insulated partitions, as disclosed herein, significantly reduces the length of furnace enclosure compared to what would be required if multiple single-position furnace cavities, each with its own insulating walls, were located adjacent to one another.

The furnace disclosed herein differs from a conventional electric furnace in other ways as well. For example, in some embodiments, the furnace has a reduced wall thickness compared to conventional electric furnace designs.

Reducing the thickness of the insulating walls of the furnace cavity improves temperature responsiveness, because the lower mass of the furnace enclosure enables faster heat-up and cool down. Wall thickness can be reduced to near-zero, at least theoretically, provided that the heating element(s) have enough power to maintain the crucible at required temperatures. Conversely, the more insulation, the less power is required to maintain a constant temperature. Furthermore, reducing furnace wall thickness results in a larger furnace cavity (for an enclosure having the same external size).

The thickness of the insulation is ultimately a tradeoff between power requirements (i.e., how much is acceptable) and temperature responsiveness. By way of comparison, the wall thickness of a conventional electric furnace, as used in a fluxer, is typically about four inches. In the illustrative embodiment, all walls/movable partitions are less than 2 inches in thickness. For example, in some embodiments, the top wall of the furnace is 1.75 inches in thickness and all other insulated walls and movable partitions have a thickness of 1 inch.

In accordance with some embodiments, certain other aspects of the fluxer are altered to reduce the impact of heat losses from the relatively thinner walls of the furnace.

One alteration is to relocate the opening of the furnace to the bottom thereof; in conventional designs, the opening is located on the side of the furnace. Furthermore, the furnace is fitted with a movable door. To the extent the furnace door is open, the fact that the opening is at the bottom helps retain the heated air therein (since hot air rises). And incorporating a furnace door that is mechanically independent of the outer door/safety shield of the fluxer enables the furnace to be kept closed during crucible loading, pouring and cooling operations, thus conserving heat.

In conventional fluxers, the trajectory of the crucible/mold holder as it travels from the loading point to the furnace cavity is typically horizontal or vertical. However, a furnace in accordance with the present teachings having its opening located at the bottom requires a non-standard trajectory. In particular, the crucible holder and mold holder must travel vertically to enter and exit the furnace and must travel horizontally to move from the loading position toward the furnace or vice-versa.

The inventors recognized that adopting an arc-like trajectory for movement of the crucible/mold holder is an efficient way to provide the requisite vertical and horizontal motion. A direct motor drive simplifies the mechanism and is sturdier than linear motion assemblies, which can seize due, for example, to chemical attacks.

In order to minimize, to the extent practical, the overall mass that is being heated in the furnace to speed heating and cooling, the structure of the crucible/mold holder has been changed from the conventional design. In particular, conventional crucible holders and mold holders accommodate multiple crucibles and molds (see, e.g., FIGS. 1 and 2). Since embodiments of the modular fusion furnace might only have one or two fusion positions operating, the extra mass of conventional crucible/molder holders would simply dull the temperature responsiveness of the fluxer.

In fact, the inventive crucible holder and mold holder is significantly different than conventional designs. The crucible holder accommodates a single crucible and the mold holder accommodates a single mold. When situated in its holder, the crucible in restricted from horizontal movement by a hoop and restricted from vertical movement by an upper and lower retainer. In the illustrative embodiment, the upper retainer is not oriented vertically (it is not orthogonal to the hoop) in at least one plane. This geometry results in an opening through which a crucible can be inserted into or removed from the crucible holder.

To load the crucible into the crucible holder, the crucible is tilted from a neutral position. When appropriately tilted, the crucible can slide between the upper retainer and the hoop. When the crucible is in the "cage" created by the bars and hoop, it is rotated back to a neutral position.

Based on the structural arrangement of the crucible holder, when it is tilted fully to pour the contents of a crucible into an underlying mold, the crucible will not fall out of the crucible holder. This is because in this rotated position, a portion of the upper edge of the crucible (now in a partially inverted position) bears on the upper retainer. Thus, the geometry of the crucible holder enables the crucible to be secure for pouring without requiring a movable locking bar or a metallic clip (which relies on metal resilience), as in conventional designs.

An illustrative embodiment of the invention is a fluxer comprising a modular electrically powered furnace having a furnace cavity characterized by a length that is variable due to the presence, within the furnace, of at least one movable insulated partition that is moved to determine the length of the furnace cavity; and a platinumware assembly, wherein the platinumware assembly comprises a rocking module and one or more instances of platinumware, each instance including a crucible holder and a mold holder, wherein the number of instances determine placement of the at least one movable insulated partition.

BRIEF DESCRIPTION OF THE DRAWINGS

FIG. 3A depicts a cutaway view of a fluxer in accordance with the illustrative embodiment of the present invention.

FIG. 4A depicts a front view of the interior of the furnace of the fluxer of FIG. 3, wherein the furnace is configured for a single fusion position.

FIG. 4B depicts a front view of the interior of the furnace of the fluxer of FIG. 3, wherein the furnace is configured for two fusion positions.

FIG. 4C depicts a front view of the interior of the furnace of the fluxer of FIG. 3, wherein the furnace is configured for three fusion positions.

FIGS. 5A-5C depict perspective views of the furnace configurations shown in FIGS. 4A through 4C, respectively.

FIG. 7A depicts a perspective view of a portion of the crucible-holder for use in conjunction with the fluxer of FIG. 3.

FIG. 7B depicts a front view of the crucible holder of FIG. 7A.

FIG. 7C depicts a side view of the crucible holder of FIG. 7A.

DETAILED DESCRIPTION

Figure 1:
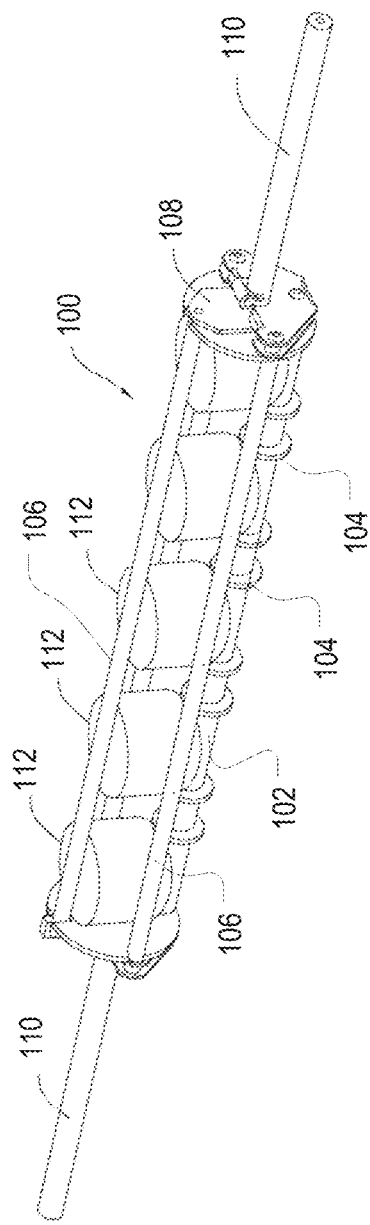
FIG. 1 depicts a prior-art crucible holder.

FIG. 3A depicts a side, cut-away view of fluxer 300 in accordance with the illustrative embodiment of the present invention.

Fluxer 300 includes enclosure 330, outer door/safety shield 332, tiltable touch screen 334, blower 336, agitation system 338, beaker well 340, crucible movement motor 342, power connection 344, furnace 346, furnace door 356, heating elements 358, and platinumware assembly 377.

Outer enclosure 330 and safety shield 332 comprise metal, such as mild steel or aluminum. The operation of safety shield 332 is mechanically independent from furnace door 356, enabling furnace 346 to be kept closed (i.e., to retain heat) during operations in which the safety shield is raised, such as crucible loading, cooling, etc.

Tiltable touch screen 334 is the user interface for the fluxer 300. Blower 336 blows air into enclosure 330 for cooling. Agitation system 338, which is a magnetic agitation system, agitates fluid in a beaker that is placed in beaker well 340 when preparing ICP (inductively coupled plasma) solutions for ICP analysis. Power connection 344 brings power to fluxer 300.

Figure 3B:
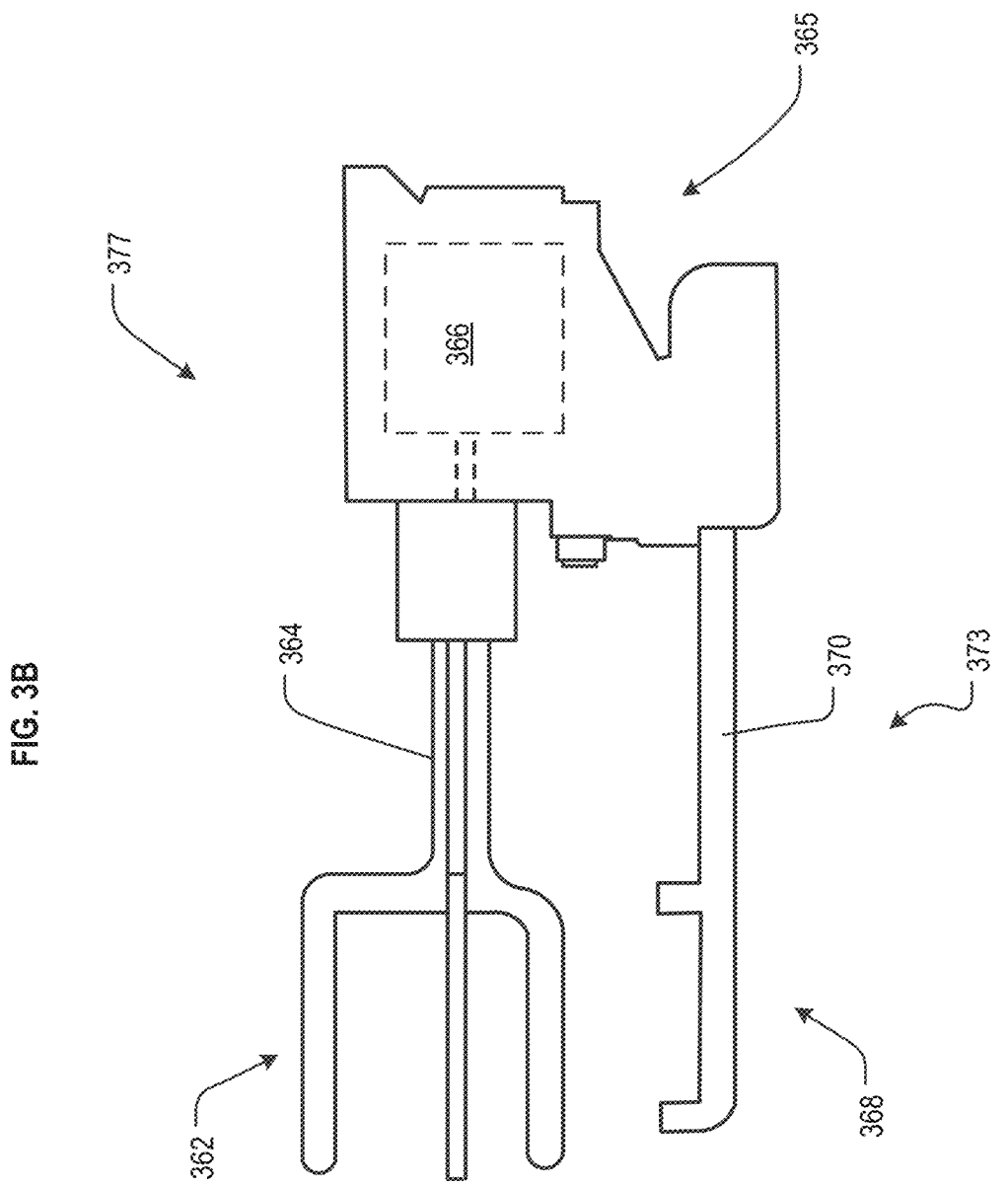
FIG. 3B depicts a side view of a platinumware assembly for use in conjunction the fluxer shown in FIG. 3A.

Referring now to FIG. 3B as well as FIG. 3A, platinumware assembly 377 includes rocking module 365 and one or more instances of "platinumware" 373. Rocking module 365 includes one or more motors 366. Each instance of platinumware 373 includes a single crucible holder 362, shaft 364, a single mold holder 368, and arms 370. As discussed later in conjunction with FIGS. 5A through 5C, rocking module 365 includes plural coupling regions that receive, as desired, one or more instances of platinumware 373.

Crucible holder 362 is coupled, via shaft 364, to motor 366. During the heating process when platinumware 373 is within furnace 346, motor 366 rocks the crucible left-to-right a few dozen degrees to provide agitation. The motor also rotates crucible holder 362 during pouring operations, wherein the contents of crucible 372 is poured into underlying mold 374.

FIG. 3A depicts crucible 372 in crucible holder 362 and mold 374 in mold holder 368; FIG. 3B depicts crucible holder and molder holder without crucible or mold. Crucible holder 362 is described in more detail later in this disclosure in conjunction with FIGS. 7A-7C and 8A-8E.

The "heart" of fluxer 300 is furnace 346. As will become clear from this disclosure, furnace 346 is non-conventional in its structure and, to a certain extent, in its operation as well.

As depicted in FIG. 3A, furnace 346 includes top wall 350 of insulation, front wall 352 of insulation, back wall 354 of insulation, and door 356, which, when closed, functions as a bottom wall of insulation. A thin metal enclosure 348 surrounds the aforementioned top wall, front wall, and back wall. Enclosure 348 also extends over the sides of furnace 346. The same thin metal that composes enclosure 348 is disposed on the outer surfaces of door 356.

Top wall 350 has the greatest thickness (of insulation). This is to address the fact that hot air rises (i.e., if all walls had the same thickness of insulation, heat loss would be greatest through the top wall). For example, in some embodiments, top wall 350 has a thickness of 1.75 inches and front wall 352, back wall 354, and door 356 have a thickness of 1 inch.

FIGS. 4A-FIG. 4C depict front views of furnace 346, with front wall 352 removed for clarity. Enclosure 348 is depicted covering top wall 350, extending down the (left and right) sides of furnace 346 to door 356. The same thin metal as used for the enclosure covers all outside surfaces of door 356. Back wall 354 includes three openings 480. Fingers 357 extending from inside surface of door 356 are dimensioned and arranged to be received by openings 480. Fingers 357 are sized so that there is a gap 481 (FIG. 4A) between the outer edge of finger 357 and the edge of opening 480. This gap enables shaft 364 of crucible holder 362 and arms 370 of mold holder 368 to pass through back wall 354 and into the interior of furnace 346 (see central fusion position).

In the embodiment depicted in FIG. 4A furnace 346 is configured with a single fusion position, which is located in the middle (left to right) of the furnace. Movable partition 482A is positioned about one-third of the length of furnace 346 from the left side of enclosure 348 and movable partition 482B is positioned about one-third of the length of furnace 346 from the right side. The movable partitions are insulating walls; in the illustrative embodiment, the thickness of each movable partition 482A and 482B is equal to the thickness of front wall 352 (not depicted in FIG. 4A), back wall 354, and door 356.

As seen from FIG. 4A, the aforementioned locations site the movable partitions on either side of the central fusion position to define furnace cavity 484-1. Three heating elements 358 are disposed horizontally, side-by-side and extend front to back just below top wall 350. In other embodiments, depending on size and element type, fewer than three heating elements or more than three heating elements may suitably be used. It is notable that there is no insulation to the left of movable partition 482A or to the right of movable partition 482B. Crucible 372 is disposed in crucible holder 362 and mold 374 is disposed in mold holder 368.

Chimney 486 vents corrosive gases from furnace cavity 484-1. The chimney can be, for example, a ceramic tube.

Figure 5A:
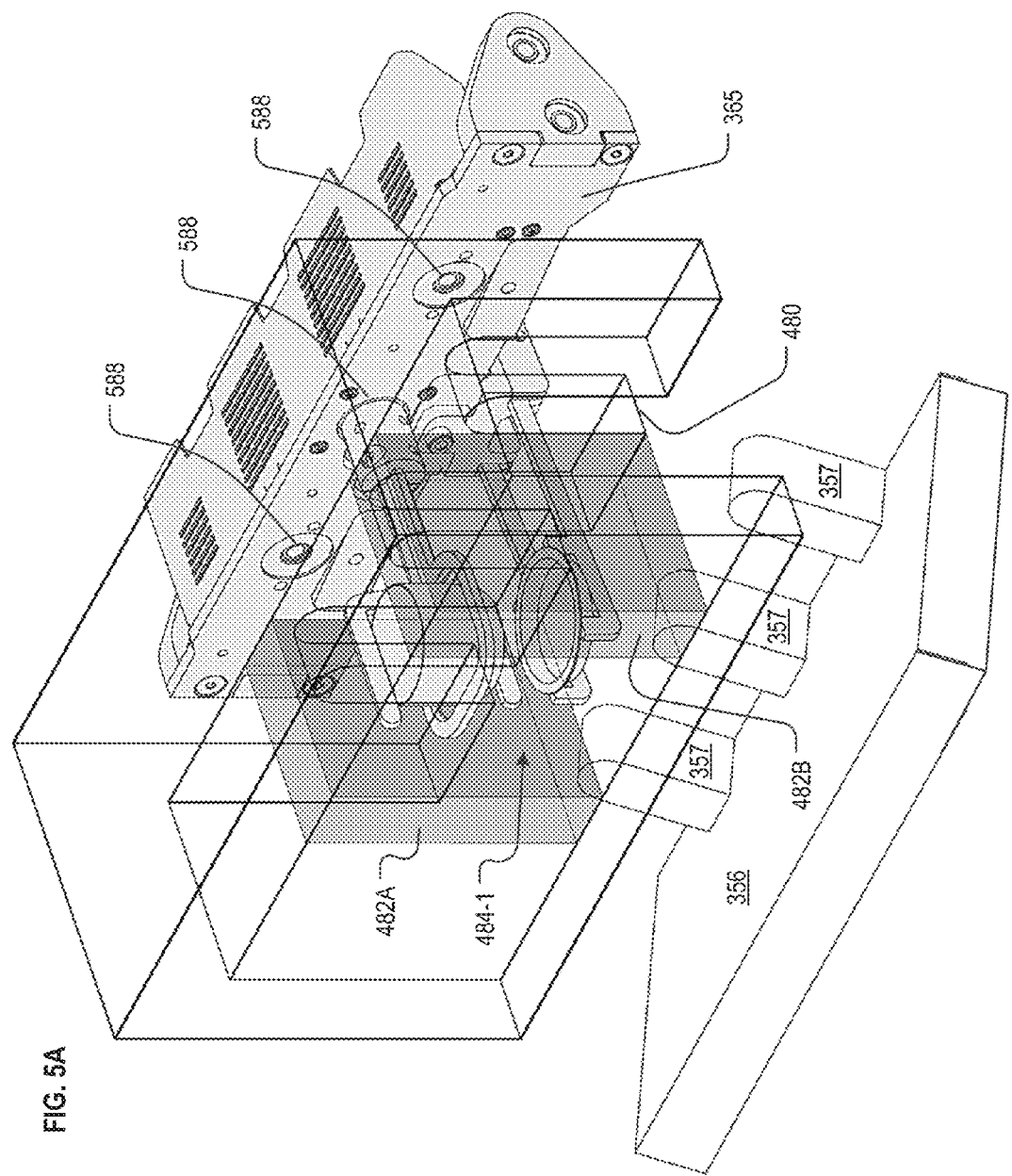

FIG. 5A depicts a perspective view of furnace 346 configured for a single fusion position (like FIG. 4A). In this figure, door 356 is depicted "open" such that fingers 357 are not engaged with openings 480. Rocking module 365 has three coupling regions 588 for receiving up to three crucible holders. Since the furnace is configured for a single fusion position, only one crucible holder is coupled to rocking module 365. Mold holders couple to rocking module 365 directly below each crucible holder. Movable partitions 482-A and 482-B are disposed on either side of the central fusion position to define furnace cavity 484-1.

In some embodiments, a single motor 366 drives all crucible holders 362 that are coupled to rocking module 356. For example, motor 366 can be installed at the central coupling region 588 while actuating a pushrod system that is able to rotate the shafts of the crucible holders that couple to the other coupling regions 588.

In the embodiment depicted in FIG. 4B, furnace 346 is configured with two fusion positions, which include the left and central positions. To accommodate these two fusion positions, movable partition 482A is sited all the way to the left side of enclosure 348 and movable partition 482B is positioned, as before, about one-third of the length of furnace 346 from the right side thereof. This positions movable partition 482A to the left of the left fusion position and movable partition 482B to the right of the central fusion position, defining furnace cavity 484-2.

Adding a fusion position requires the addition of certain other elements to furnace 346. In addition to a second crucible holder 362 and second mold holder 368, two heating elements 358, a power switching device (not depicted) that controls power to the heating elements (e.g., snap-in solid state relays, etc.), and a second chimney 486 and are added above the left fusion position. It will be understood that in some other embodiments, partitions 482A and 482B are positioned so that the furnace cavity includes the central fusion position and the right fusion position, rather than the left fusion position.

Figure 5B:
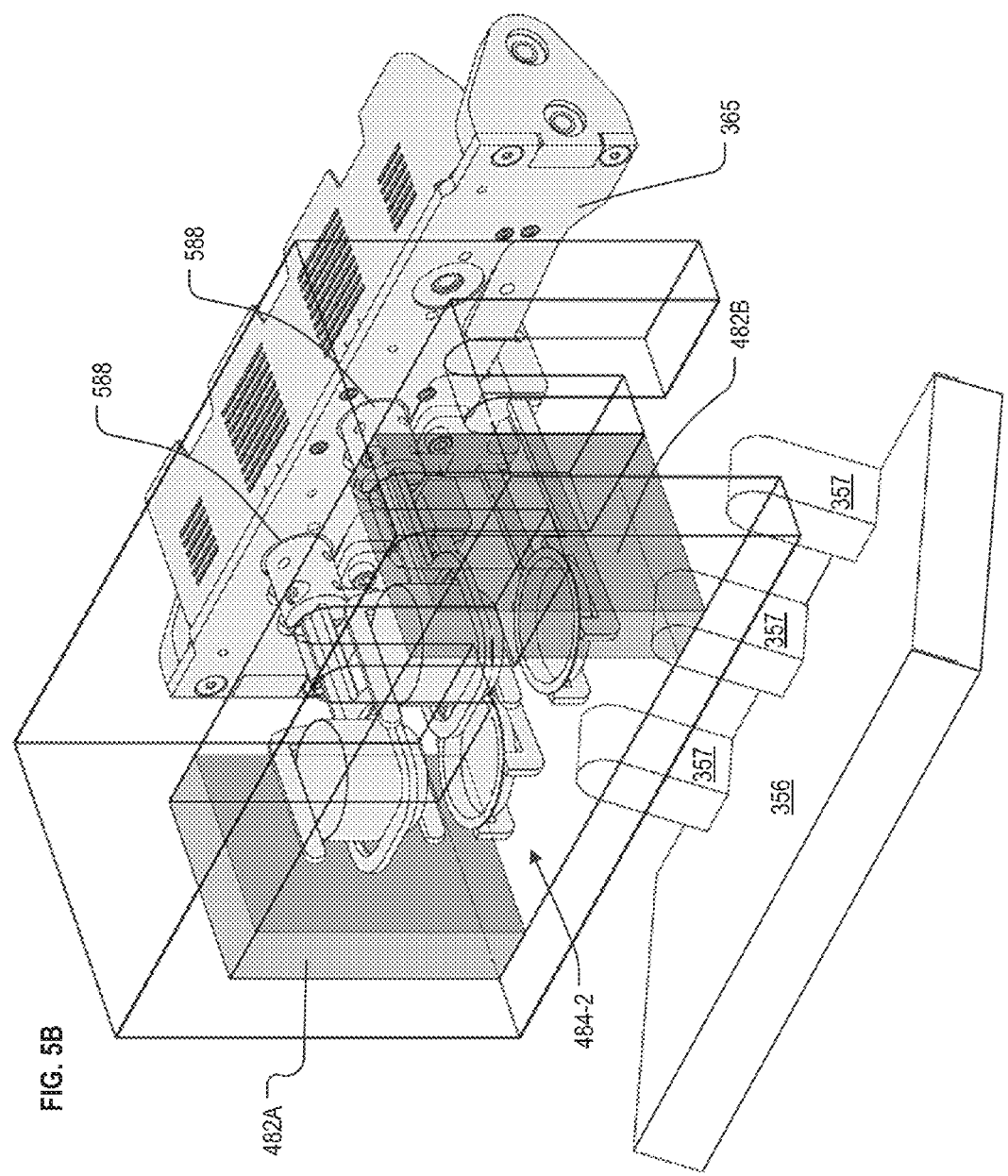

FIG. 5B depicts a perspective view of furnace 346 configured for two fusion positions (like FIG. 4B). Rocking module 365 receives two instances of crucible holders and mold holders at two of coupling regions 588. Movable partition 482-A is sited at the left end of the furnace and movable partition 482-B is sited on the right side of the central fusion position to define furnace cavity 484-2.

In the embodiment depicted in FIG. 4C, furnace 346 is configured so that all three fusion positions are operational. To accommodate three fusion positions, movable partition 482A is positioned all the way to the left side of enclosure 348 and movable partition 482B is positioned all the way to the right side of the enclosure. This positions movable partition 482A to the left of the left fusion position and movable partition 482B to the right of the right fusion position, defining furnace cavity 484-3.

As before, to accommodate the third fusion position, the same elements are added to furnace 346 (i.e., a third crucible holder 362, third mold holder 368, two heating elements 358, a power switching device [not depicted], and a third chimney 486).

FIG. 5C depicts a perspective view of furnace 346 configured for three fusion positions (like FIG. 4C). Rocking module 365 receives three instances of crucible holders and mold holders. Movable partitions 482A and 482B are sited at the left and right ends of the furnace to define furnace cavity 484-3.

Although two heating elements are added for each additional fusion position in the illustrative embodiment, in other embodiments, a greater or lesser number of heating elements could be added as a function of element size and type, as well as furnace size.

Thus, through the use of movable partitions 482A and 482B, a variable-size furnace cavity is created. The size of the furnace cavity is appropriately altered to accommodate a specific number of fusion positions. Since the cavity is no larger than it needs to be, and since rocking module 365 has the capability to couple to a desired number of crucible holders and mold holders (up to its maximum capability), no more mass than is necessary is being temperature cycled. This improves the temperature responsiveness of fluxer 300.

Also, because of the use of movable partitions, as opposed to the use of plural, individual, adjacent furnace cavities, only two side insulating walls, as opposed to four (to create three cavities), are required. This reduces the amount of space required for a given number of fusion positions.

Although the illustrative embodiment depicts furnace 346 and rocking module 365 with a maximum of three fusion positions, it is to be understood that in other embodiments, as desired, a furnace and rocking module may have a maximum two fusion positions, or a maximum of more than three fusion positions, such as four, five, etc. It is notable that even if the furnace has a capability for accommodating more than three fusion positions, two movable partitions can still be used to create a furnace cavity of the required size.

In some further embodiments, rather than using two movable partitions, a fluxer having a variable-size furnace cavity includes only a single movable partition. In such embodiments, one of the movable partitions is replaced by a fixed partition; that is, a side wall. For example, with reference to FIG. 4B, movable partition 482A could be a fixed wall. To create a single fusion position, movable partition 482B is moved to a position that is about one-third of the length of enclosure 348 away from the left wall, so that the furnace cavity includes only the left fusion position. To accommodate two fusion positions, movable partition 482B is moved to the position in which it appears in FIG. 4B. And to accommodate three fusion positions, movable partition 482B is moved all the way to the right.

Returning again to FIG. 3A, furnace 346 opens at the bottom thereof, rather than at the side as in conventional designs. Thus, door 356 serves as the "bottom" wall of the furnace. Door 356 is (automatically) movable; the door is shown ajar in FIG. 3A. The door is actuated by a motor (not depicted), which drives a belt (not depicted) that rotates pulley 359. The pulley has lever 360 attached thereto. Door 356 is pivotally coupled to lever 360 at a location close to, but not at, the end of the lever. A bearing (not depicted) extends from the back (right side of the figure) of the non-visible side of door 356 and engages slot 375. This arrangement forces the desired (rotational) movement between lever 360 and door 356. Rotating the pulley clockwise causes door 356 to open by dragging the door to the left to completely clear the furnace opening to provide access to the interior thereof. To close the door, the pulley is rotated counterclockwise. Pin 361 catches the edge of door 356, forcing it upward near the end of the movement to seal the opening of furnace 346.

To the extent that door 356 is open, the fact that the opening of the furnace is located at the bottom thereof helps to retain the heated air therein. And incorporating door 356, which is mechanically independent of the opening/closing of safety shield 332, enables the furnace to be kept closed during crucible loading, pouring and cooling, thereby retaining heat.

Figure 6:
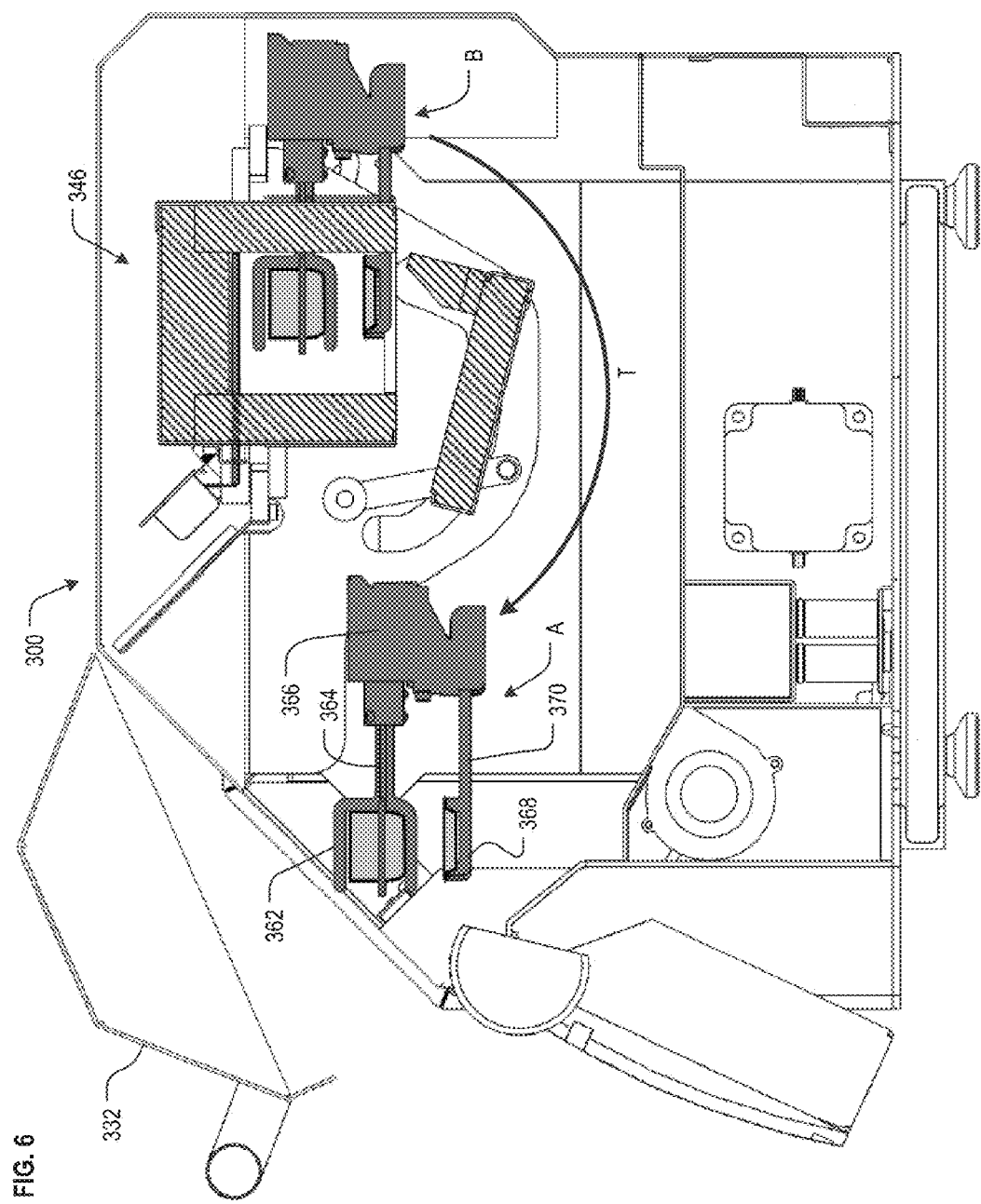
FIG. 6 depicts the fluxer of FIG. 3, showing the movement of a crucible holder and a mold holder between a loading position and an operating position in accordance with the present teachings.

Referring now to FIG. 6, platinumware assembly 377 is shown in two positions: position "A," which is the loading position (i.e., for loading crucibles 372 and molds 374) near the safety shield 332 and position "B," which places platinumware 373 in furnace 346. In conventional fluxers, the trajectory of the platinumware (embodied as in FIGS. 1 and 2) as it travels from the loading point to the furnace cavity is typically horizontal or vertical. As a consequence of the bottom-opening furnace of the illustrative embodiment, a non-standard trajectory for platinumware assembly 377 is required. In particular, it must travel vertically to enter and exit the furnace cavity and horizontally to move from the loading position toward the furnace or vice-versa.

In accordance with embodiments of the present invention, platinumware 373 exits furnace 346 in arc-like trajectory T. This non-linear trajectory combines the vertical motion needed to exit the furnace with the horizontal motion required to bring platinumware assembly 377 close to the user for loading crucibles 372 and molds 374. In some embodiments, this non-linear movement of platinumware assembly 377 is accomplished by a mechanism that provides sufficient torque to move the platinumware assembly and keeps the platinumware 373 horizontal. In an exemplary embodiment, the mechanism includes two motors that drive a belt that rotates a pulley coupled to a lever. A double lever arrangement keeps the platinumware horizontal. Direct motor drive simplifies the mechanism while being sturdier than linear motion assemblies, which can seize due, for example, to chemical attacks.

Figure 2:
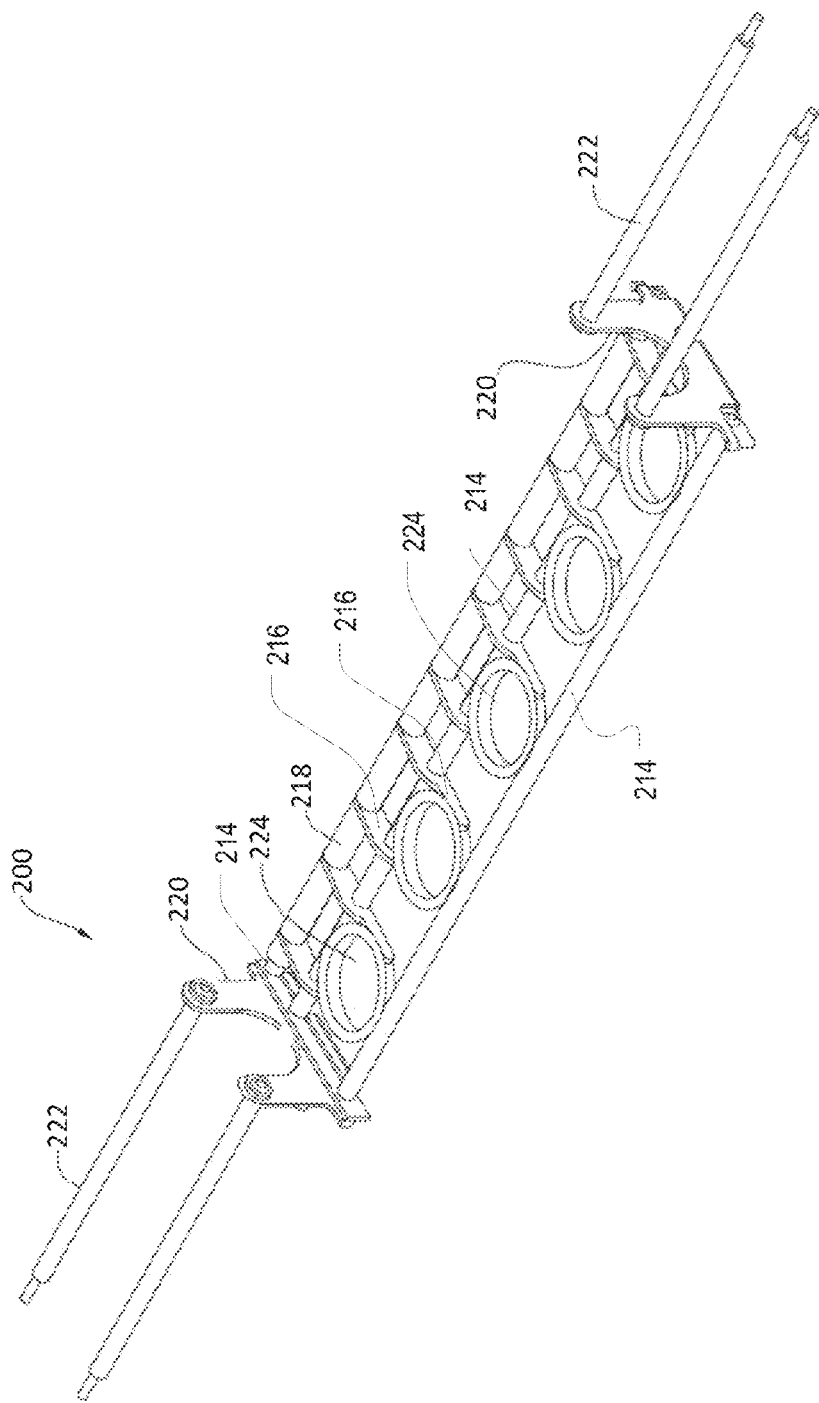
FIG. 2 depicts a prior-art mold rack.

As a consequence of the design and operation of furnace 346, platinumware 373 for use in conjunction with the illustrative embodiment must be significantly different than conventional designs, as shown in FIGS. 1 and 2.

FIG. 7A depicts crucible-holder 362. Crucible holder 362 includes horizontally-oriented retainer 790, upper retainer 792, and lower retainer 796. Horizontally-oriented retainer 790 restricts crucible 372 from any horizontal movement. Upper retainer 792 prevents crucible 372 from falling out of crucible holder 362 during pouring operations and lower retainer 796 supports crucible 372 against gravity during loading and heating operations.

In the illustrative embodiment, horizontally-oriented retainer 790 is a hoop (hereinafter "hoop 790"). In a neutral position, the hoop is oriented horizontally. Upper retainer 792 includes rise portion 793 and retaining bar 794. The rise portion is located on the hoop at its midline and supports retaining bar 794 over the hoop and substantially parallel thereto. Lower retainer 796 includes drop portion 797 and retaining bar 798. The drop portion is located on the hoop at its midline and supports retaining bar 798 below the hoop and substantially parallel thereto.

FIG. 7B, which is a front view of FIG. 7A (crucible 372 not shown) and FIG. 7C, which is a side view of FIG. 7A (crucible 372 not shown), provide additional information about the structure of crucible holder 362. As can be seen from FIG. 7B, neither rise portion 793 nor drop portion 797 are orthogonal to hoop 790. The angle, α, subtended between rise portion 793 and hoop 790, is greater than 90 degrees. As discussed further below in conjunction with FIGS. 8A-8F, this structural arrangement facilitates insertion and removal of crucible 372 from crucible holder 362. Although drop portion 797 is depicted in the illustrative embodiment as being co-linear with rise portion 793, in some other embodiments, the drop portion is orthogonal to hoop 790 (i.e., extending straight down in FIG. 7B).

As can be seen from FIG. 7C, hoop 790 is disposed relatively closer to retaining bar 798 than retaining bar 794. In conjunction with obtuse angle α, this arrangement facilitates insertion and removal of crucible 372 from crucible holder 362.

Based on the arrangement of horizontally-oriented retainer 790, upper retainer 792, and lower retainer 796, when crucible holder 362 tilts fully to the right (c.a. 120 to 130 degrees by rotation about axis A-A in direction P (FIG. 7A)) for pouring the contents of crucible 372, the crucible will not fall through the space between retaining bar 794 and hoop 790. This is because in this fully tilted position, a portion of the upper edge of crucible 372 (which would be in a partially inverted position) bears on retaining bar 794. Thus, in the illustrative embodiment, the geometry of the crucible holder enables the crucible to be secure for pouring without requiring a movable locking bar or a metallic clip (which relies on metal resilience) as in conventional designs.

The angle α (FIG. 7B) is a function of crucible dimensions (height and diameter) relative to the size of hoop 790 and height of rise portion 793 of upper retainer 792. In other words, there is nothing particularly significant about the value of angle α; it is simply the angle that results as a consequence of the sizes of the various elements noted above. There are a number of standard sizes for crucibles. Thus, in accordance with the illustrative embodiment, to the extent that a choice of crucible is available, a crucible should be selected that has a height-to-width ratio that results in a "securing geometry" when used in conjunction with the crucible holder. As used in this disclosure and the appended claims, the term "securing geometry" means that a crucible can be secured for pouring within the crucible holder without requiring a locking function (e.g., movable locking bar, metallic clip, etc.).

Figure 8B:
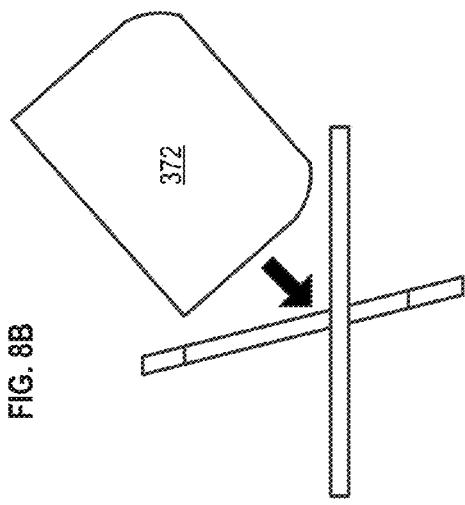
FIGS. 8A-8E depict, via a sequence of front views, a method by which a crucible is positioned within the crucible holder of FIG. 7A.
Figure 8E:
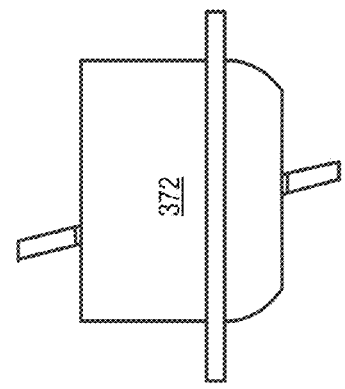
Figure 8D:
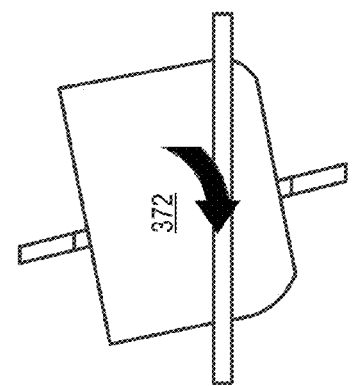
Figure 8A:
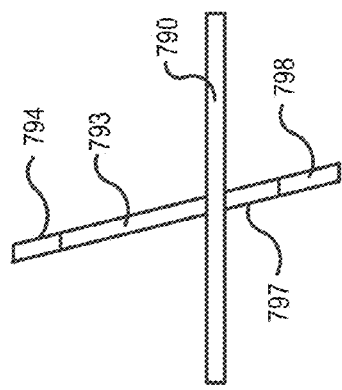
Figure 8C:
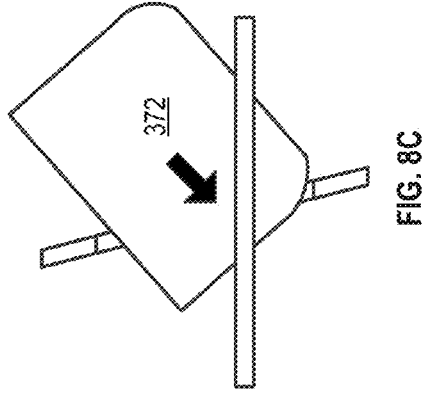

The loading motion of crucible 372 is depicted in FIGS. 8A through 8E via front views of crucible holder 362. FIG. 8A depicts a front view of crucible holder 362 sans crucible 372. As depicted in FIGS. 8B and 8C, crucible 372 is initially tilted so that it can be slid between retaining bar 794 and hoop 790. When the crucible is in the "cage" created by the various bars and hoop, it is rotated, as depicted in FIG. 8D, toward an un-tilted position. FIG. 8E depicts crucible 372 in its final, fully supported and neutral position within crucible holder 362.

It is to be understood that the disclosure teaches just one example of the illustrative embodiment and that many variations of the invention can easily be devised by those skilled in the art after reading this disclosure and that the scope of the present invention is to be determined by the following claims.

What is claimed:

1. A fluxer comprising a modular electrically powered furnace, wherein the modular electrically powered furnace comprises:
    a first wall having a plurality of spaced-apart openings, each opening dimensioned and arranged to enable a crucible holder and a mold holder to extend through the first wall and into the furnace, each such opening thereby defining a potential fusion position; and
    a furnace cavity having a variable length, wherein the furnace cavity is defined, in part, by the first wall and two partitions, at least one of which partitions being movable, wherein a length of the first wall defines a maximum furnace cavity length and moving the at least one movable partition along the length of the first wall varies the length of the furnace cavity, wherein, as the length of the furnace cavity varies, more or fewer of the spaced-apart openings and, hence, fusion positions, are encompassed within the length of the furnace cavity.

2. The fluxer of claim 1 wherein each one of the two partitions are movable.

3. The fluxer of claim 1 wherein the furnace cavity is further defined by a top wall, a front wall, and an automatic insulated door, wherein the door, when closed, abuts a bottom of the front wall and the first wall, thereby functioning as a bottom wall of insulation.

4. The fluxer of claim 3 wherein the door comprises fingers that are received in the spaced-apart openings when the door is closed.

5. The fluxer of claim 1 further comprising heating elements, wherein one or more heating elements are associated with each fusion position, and wherein the heating elements associated with a respective fusion position are present in the modular electrically powered fusion furnace only when the respective fusion position is encompassed by the furnace cavity.

6. The fluxer of claim 1 further comprising a platinumware assembly, wherein the platinumware assembly comprises a rocking module, wherein the rocking module has plural coupling regions for receiving plural crucible holders, one crucible holder per coupling region, and wherein each crucible holder receives a single crucible, and further wherein each crucible holder that is coupled to the rocking module couples to a motor.

7. The fluxer of claim 6 wherein the crucible holder is characterized by a securing geometry with respect to a received crucible.

8. The fluxer of claim 7 wherein the crucible holder comprises a hoop, an upper retainer, and a lower retainer.

9. The fluxer of claim 6 wherein the rocking module is configured to receive plural mold holders below the plural crucible holders.

10. The fluxer of claim 9 further comprising a mechanism that moves the platinumware assembly in a non-linear path between a loading position, at which one or more crucibles and molds are loaded into respective crucible holders and mold holders, and a heating position within the modular electrically powered furnace.

11. The fluxer of claim 3 wherein the top wall, the front wall, the first wall, the door, and the two partitions have a thickness less than 2 inches, and wherein the top wall has a thickness that is greater than the thickness of the front wall, the first wall, the automatic insulated door, and the two partitions.

12. A fluxer comprising:
a modular electrically powered furnace having a furnace cavity characterized by a length that is variable, wherein the furnace cavity is defined by a top wall of insulation, a front wall of insulation, a back wall of insulation, an automatically movable insulated door that functions as a bottom wall of insulation, and first and second movable partitions, wherein placement of the first and second movable partitions sets the length of the furnace cavity; and
a platinumware assembly, wherein the platinumware assembly comprises a rocking module and one or more instances of platinumware, each instance including a crucible holder and a mold holder, wherein the rocking module has plural coupling regions for receiving one or more crucible holders, one crucible holder per coupling region, and wherein each crucible holder receives a single crucible, and wherein each crucible holder that is coupled to the rocking module couples to a motor.

13. The fluxer of claim 12 wherein the back wall of insulation comprises a plurality of spaced-apart openings that extend part way up the back wall and all the way down to the automatically movable insulated door, wherein each spaced-apart opening is capable of receiving one instance of platinumware and, when so received, defines a fusion position.

14. The fluxer of claim 13 wherein the first and second movable partitions are movable to encompass a desired number of fusion positions, the furnace cavity therefore being no larger than is required to accommodate the desired number of fusion positions.

15. The fluxer of claim 14 wherein there are at least three spaced apart openings and the movable partitions are movable to define a furnace cavity having any of: one fusion position, two fusion positions, or three fusion positions, wherein the furnace cavity does not include any openings that do not receive an instance of the platinumware.

16. A fluxer comprising
a modular electrically powered furnace having a furnace cavity characterized by a length that is variable due to the presence, within the furnace, of at least one movable insulated partition that is moved to determine the length of the furnace cavity; and
a platinumware assembly, wherein the platinumware assembly comprises a rocking module and one or more instances of platinumware, each instance including a crucible holder and a mold holder, wherein the number of instances determine placement of the at least one movable insulated partition.

17. The fluxer of claim 16 wherein the crucible holder is characterized by a securing geometry with respect to a received crucible.

18. The fluxer of claim 17 wherein the crucible holder comprises a hoop, an upper retainer, and a lower retainer.

19. The fluxer of claim 16 further comprising a mechanism that moves the platinumware assembly in a non-linear path between a loading position, at which one or more crucibles and molds are loaded into respective crucible holders and mold holders, and a heating position within the modular electrically powered furnace.

20. The fluxer of claim 16 wherein the fluxer further comprises:
a safety shield that controls access to an interior of the fluxer; and
an automatically operated insulated door for controlling access to the interior of the modular electrically powered furnace, wherein the safety shield is operable independently of the insulated door so that the modular electrically powered furnace can remain closed while the interior of the fluxer is accessed.

* * * * *